United States Patent [19]

Vanderspurt

[11] 4,020,116

[45] Apr. 26, 1977

[54] VAPOR PHASE CATALYTIC PROCESS FOR PREPARING ALPHA, BETA-ETHYLENICALLY UNSATURATED ALCOHOLS

[75] Inventor: Thomas H. Vanderspurt, Gillette, N.J.

[73] Assignee: Celanese Corporation, New York, N.Y.

[22] Filed: May 12, 1976

[21] Appl. No.: 685,610

[52] U.S. Cl. .......................... 260/638 B; 252/444; 252/449; 252/461; 260/601 R
[51] Int. Cl.² ........................................ C07C 29/14
[58] Field of Search ................................ 260/638 B

[56] References Cited

UNITED STATES PATENTS

| 2,763,696 | 9/1956 | Finch et al. | 260/638 B |
| 2,767,221 | 10/1956 | Ballard et al. | 260/638 B |
| 3,284,517 | 11/1966 | Rylander et al. | 260/638 B |
| 3,655,777 | 4/1972 | Rylander et al. | 260/638 B |

OTHER PUBLICATIONS

Broadbent et al., "J. Org. Chem." vol. 24 (1959), pp. 1847–1854.

Davenport et al., "Ind. & Eng. Chem.", vol. 60 (1968), pp. 10–19.

Primary Examiner—Joseph E. Evans

[57] ABSTRACT

There is disclosed a selective process for preparing alpha, beta-ethylenically unsaturated alcohols such as allyl alcohol in the vapor phase. This process comprises reacting an alpha, beta-ethylenically unsaturated aldehyde such as acrolein with a hydrogen-containing gas in the vapor phase in the presence of a supported partially decomposed rhenium catalyst. A preferred catalyst comprises the partial decomposition product of rhenium decacarbonyl and a large pore diameter support material such as controlled pore size type glass.

A particularly selective vapor phase reduction results when the reaction is carried out in the presence of a critical amount of a selective catalyst poison such as carbon monoxide or carbon disulfide. This selective catalyst poison substantially inhibits the conversion of reactant to undesired product but does not substantially interfere with the conversion of reactant to the desired products.

14 Claims, No Drawings

VAPOR PHASE CATALYTIC PROCESS FOR PREPARING ALPHA, BETA-ETHYLENICALLY UNSATURATED ALCOHOLS

BACKGROUND OF THE INVENTION

I. Field of the Invention

This invention relates generally to processes for preparing unsaturated alcohols. More particularly, the invention relates to vapor phase processes for preparing alpha, beta-ethylenically unsaturated alcohols from alpha, beta-ethylenically unsaturated aldehydes by direct hydrogenation.

II. Summary of the Prior Art

Processes for preparing alpha, beta-ethylenically unsaturated alcohols by the hydrogen reduction of alpha, beta-ethylenically unsaturated carbonylic compounds may be represented by the following equation:

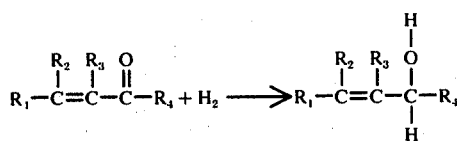

wherein $R_1$, $R_2$, $R_3$ and $R_4$ may be hydrogen or lower alkyl. Such, or similar processes, are described, for example, in U.S. Pat. No. 2,763,696 (Finch et al.), U.S. Pat. No. 2,767,221 (Ballard et al.), U.S. Pat. No. 3,655,777 (Rylander et al.), and Broadbent et al., J. Org. Chem. 24, 1844 – 54 (1959).

Processes for the vapor phase hydrogenation of alpha, beta-ethylenically unsaturated carbonylic compounds to alpha, beta-ethylenically unsaturated alcohols are disclosed in U.S. Pat. No. 2,763,696 and 2,767,221 but such processes suffer from the disadvantages of low selectivity as well as the need for relatively high reaction temperatures and pressures. Further, those processes which carry out the hydrogenation of alpha-beta unsaturated aldehydes in a liquid phase may be accompanied by undesirable polymerization reactions.

The search has continued for improved processes for preparing alpha, beta-ethylenically unsaturated alcohols by the vapor phase hydrogenation of alpha, beta-ethylenically unsaturated aldehydes. This invention was made as a result of that search.

OBJECTS AND SUMMARY OF THE INVENTION

Accordingly, a general object of the present invention is to avoid or substantially alleviate the above problems of the prior art.

A more specific object of the present invention is to provide a selective process for preparing alpha, beta-ethylenically unsaturated alcohols from alpha, beta-ethylenically unsaturated aldehydes.

Another object of the present invention is to provide a process for preparing alpha, beta-ethylenically unsaturated alcohols from alpha, beta-ethylenically unsaturated aldehydes under moderate conditions of temperature and pressure.

Other objects and advantages of this invention will become apparent from the following summary and description of the preferred embodiments of the present invention.

The present invention provides a selective vapor phase process for preparing alpha, beta-ethylenically unsaturated alcohols. This process comprises reacting an alpha, beta-ethylenically unsaturated aldehyde with a hydrogen-containing gas in the vapor phase in the presence of a supported rhenium catalyst comprising a rhenium compound having a formal oxidation number on the rhenium atom of three or less and a support for the rhenium compound, the support having average pore diameters greater than about 40 angstroms.

The essence of the present invention is the discovery that unsaturated alcohols may be selectively prepared by reacting unsaturated aldehydes with a hydrogen-containing gas in the vapor phase in the presence of a supported rhenium catalyst under moderate conditions of temperature and pressure. The supported rhenium catalyst comprises (1) a rhenium compound having a formal oxidation number on the rhenium atoms of three or less and (2) a support for this rhenium compound, wherein the support has average pore diameters greater than about 40 Angstroms.

A primary object of the present invention is the use of the partial decomposition product of rhenium decacarbonyl as the rhenium compound in the catalyst composition. The use of this particular rhenium compound results in higher selectivity and conversion then when hydrogen reduced rhenium oxides are employed in the catalyst composition.

Another primary aspect of the present invention is the use of a selective catalyst poison in combination with the supported rhenium catalyst. This selective catalyst poison inhibits the formation of undesirable by-products but does not to any great extent inhibit the formation of the desired unsaturated alcohol, thus leading to selectivities and conversions which are higher than would be possible in the absence of such selective catalyst poisons.

DESCRIPTION OF THE PREFERRED EMBODIMENTS

As indicated hereinabove, the present process comprises reacting alpha, beta-ethylenically unsaturated aldehydes with a hydrogen-containing gas in the vapor phase in the presence of a supported rhenium catalyst. Any alpha, beta-ethylenically unsaturated aldehyde which will substantially all remain in the vapor phase under the conditions of temperature and pressure described hereinbelow may be used in the present process. Preferred alpha, beta-ethylenically unsaturated aldehydes have a structure which may be represented by the following general formula:

wherein the various radicals indicated by $R_1$, $R_2$ and $R_3$ may be the same as or different from one another and represent either hydrogen atoms or methyl groups. Representative aldehydes which may be selectively reduced in accordance with the process of the present invention include the following:

   acrolein (propenal)

-continued

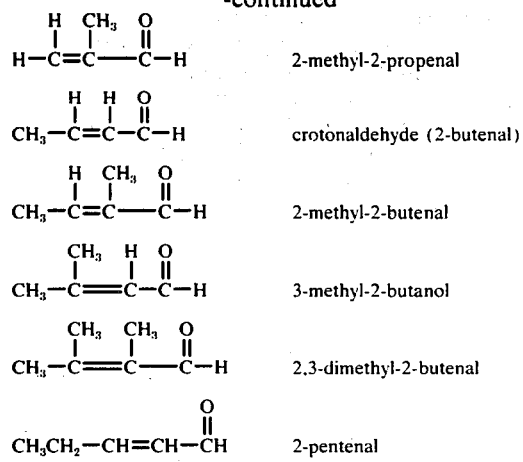

$$\underset{H}{\overset{H}{|}}\underset{|}{\overset{CH_3}{|}}\underset{}{\overset{O}{\|}}$$
H—C=C——C—H      2-methyl-2-propenal CH₃—C=C—C—H      crotonaldehyde (2-butenal)

CH₃—C=C——C—H      2-methyl-2-butenal

CH₃—C≡C—C—H      3-methyl-2-butanol

CH₃—C≡C——C—H      2,3-dimethyl-2-butenal

CH₃CH₂—CH=CH—CH      2-pentenal

Of course, mixtures of alpha, beta-ethylenically unsaturated aldehydes may also be used.

The alpha, beta-ethylenically unsaturated aldehydes may be reacted with substantially pure hydrogen gas or other gaseous mixtures containing hydrogen gas. Such gaseous mixtures may in addition to hydrogen gas also include inert gases such as nitrogen, carbon dioxide and the like.

The term "hydrogen-containing gas" is used in the present specification to include both substantially pure hydrogen gas as well as hydrogen-containing gaseous mixtures.

The molar ratio of substantially pure hydrogen gas to unsaturated aldehyde may be generally from about 1 to 1 to about 200 to 1, typically from about 10 to 1 to about 100 to 1, preferably from about 20 to 1 to about 75 to 1. When a molar ratio appreciably below 1 to 1 is employed, then hydrogenation may not be complete, the selectivity may decrease, and the products may not be carried away from the catalyst at a speed sufficient to prevent by-product formation. When this ratio is appreciably above 200 to 1, then operation costs are increased because of, e.g., added equipment costs resulting from the large excess of hydrogen that must be handled in the process stream.

The supported rhenium catalyst that may be used in the process of the present invention comprises a rhenium compound and a support for the rhenium compound. The term "rhenium compound" is meant to include e.g., rhenium metal and any rhenium compound where the formal oxidation number on the rhenium atom is three or less. More specifically the rhenium compounds contemplated within the scope of the present invention include those compounds which when subjected to conditions hereinafter described undergo a partial decomposition to a state wherein the surface of these compounds has present thereon a plurality of coordination vacancies which are capable of inducing the selective conversion of the alpha, beta-ethylenically unsaturated aldehydes to alpha, beta-ethylenically unsaturated alcohols. By way of explanation it is believed that by subjecting these compounds to increased temperature and pressure under a hydrogen atmosphere a cluster of 2 or more rhenium atoms joined by metal-metal bonds is formed. This cluster is capable of coordinating with a plurality of certain ligands such as carbonyl molecules while simultaneously also being capable of forming metal-olefin or metal-aromatic π bond complexes. It is believed that such coordination occurs at the surface of the rhenium metal clusters.

It is an aspect of the present invention that when the rhenium containing compounds included within the scope of the presently claimed invention are treated in accordance with the procedures outlined below the partial decomposition products resulting therefrom provide and maintain a sufficient number of coordination vacancies so as to enable these decomposition products to induce, through catalytic interaction at these vacancies, the selective conversion of the alpha, beta-ethylenically unsaturated aldehyde to its respective alpha, beta-ethylenically unsaturated alcohol.

Thus, representative examples of suitable compounds which may be thermally decomposed include rhenium compounds which have complexed therewith a plurality of carbonyl molecules, i.e., (CO) (e.g., 10 or less) as well as short chain (e.g., 1 to 10 carbon atoms) linear olefinic, cyclo olefinic, and aromatic molecules.

Specific compounds which exemplify those which may be utilized to provide the desired rhenium decomposition product include those compounds which possess the following initial structures such as $Re_2(CO)_{10}$ (rhenium decacarbonyl), $\pi$-$C_5H_5Re(CO)_3$ ($\pi$-cyclopentadienyl carbonyl rhenium I), ($\pi$-$C_5H_5)_2ReH$ (bis- $\pi$-0 cyclopentadienyl rhenium III hydride), $C_{10}H_{11}Re(CO_2)$, and $R\,Re\,(CO)_5$ wherein R is a member selected from the group consisting of phenyl, methyl, and perfluropropyl. Mixtures of two or more rhenium compounds may also be used.

A particularly preferred rhenium compound for use with a support of the type described herein in the process of the present invention includes a partially decomposed rhenium decacarbonyl catalyst.

Rhenium decacarbonyl $[Re_2(CO)_{10}]$ is especially convenient as a starting material for the production of the partially decomposed species because it is relatively stable and not very sensitive to air or moisture prior to use and it is readily soluble in common and preferred solvents such as tetrahydrofuran. Other rhenium compounds described herein may have special merits when used with a particular support for a particular application.

The use of this partially decomposed rhenium decacarbonyl as the rhenium compound in the process of the present invention is particularly preferred in that it has been found unexpectedly that this particular catalyst results in improved selectivity and conversion over other supported rhenium catalysts such as rhenium metal or undecomposed rhenium decacarbonyl. The use of this partially decomposed rhenium carbonyl compound will result in higher selectivity and conversion than would result from the use of a rhenium compound prepared by reducing, e.g., rhenium heptoxide with hydrogen as described, for example, in the article by Broadbent et al., discussed hereinabove. This higher selectivity and conversion is unexpected since both compounds apparently contain rhenium having an oxidation number of zero and thus may be expected to have similar catalytic activity.

In this specification, by the term "conversion" is meant the percent of unsaturated aldehyde (e.g., acrolein) which is converted to all products (e.g., allyl alcohol, n-propyl alcohol, etc.) whereas by the term "selectivity" is meant the percent of converted unsaturated aldehyde (e.g., converted acrolein) that goes to the desired product (e.g., allyl alcohol).

The support for the rhenium compound useful in the present invention may be any acceptable pore containing support or mixture of two or more such supports which is initially free of significant amounts of catalyst poisons capable of influencing the conversion reaction. This allows for the addition of selective poison in controlled amounts. The catalyst supports may have average pore diameters of from about 40 A to about 4800 A, preferably from about 100 to about 1200 A, and most preferably from about 110 to about 140 A (e.g., 126 A). Catalyst supports having average pore diameters lower than about 40 A may result in condensation of the unsaturated aldehyde in the pores of the support. This consensed unsaturated aldehyde may polymerize within the support causing loss of activity to the catalyst. Supports having excessively large average pore diameters (e.g., greater than 4800 A) will possess a low surface area and therefore the rhenium catalyst supported thereon will evidence a low catalytic activity. Pore size is of considerable importance since as the pore size decreases the temperature at which undesirable capillary condensation can occur at a given partial pressure of aldehyde also decreases. Thus, higher temperatures would be required to maintain the aldehyde in a vapor state.

The catalyst support may be, for example, such pore containing materials as activated carbon silica, controlled pore size type pore glass, controlled pore size type $T_iO_2$ ceramic, controlled pore size type $ZrO_2$ ceramics. Controlled pore size type supports are preferred since they have high surface areas per unit weight or volume and their use assures that greater than 90% of the pores have a size within ± 10% of the stated size thereof virtually eliminating the effect of unacceptably small pores.

The average pore diameter may be determined by mercury porisimetry.

Such procedures are well known and are outlined in C. Orr, J. Dallavalle *Fine Particle Measurement* (1960) which is herein incorporated by reference. Briefly, the penetration of a nonwetting liquid such as mercury under the application of pressure is described by two equations developed by Ritter and Drake (1945).

The surface tension of the liquid opposes entrance into a small pore if the liquid has an angle of contact with the solid material, greater than 90 deg. This is the common phenomenon of capillary depression. The external pressure must overcome this opposition. If the cross section of a pore is circular, the surface tension, $\sigma$, acts along the circle of contact for a length equal to the perimeter of the circle. This force is $2\pi r\sigma$, if $r$ is the pore radius. The force tending to squeeze the liquid out of the pore, normal to the plane of the circle of contact, may be written $-2\pi r\sigma \cos\theta$, where $\theta$ is the contact angle (since for $\theta > 90°$ the term $-2\pi r\sigma \cos\theta$ is intrinsically positive). The opposing force, due to the pressure, acts over the area of the circle of contact and is $\pi r^2 p$. At equilibrium the opposing forces are equal; thus $$1 \quad -2\pi r\sigma \cos\theta = \pi r^2 p \tag{1}$$

$$2 \quad pr = 2\sigma \cos\theta \tag{2}$$

Equation 2 shows that no pores will be penetrated by a nonwetting liquid under zero pressure. At a pressure of 25 psi, pores with a diameter of about 8.6 $\mu$ will be penetrated. As the pressure is increased, the amount of liquid forced into the pores increases at a rate which is proportional to the differential pore volume of the pores, the size of which corresponds to the instantaneous pressure. Thus, increasing the pressure on a material having a given pore-size distribution results in a unique pressure-volume curve; conversely, a given pressure-volume curve affords a determination of the pore-size distribution.

If the volume of all pores having radii between $r$ and $r + dr$ is $dV$, then $$3 \quad dV = D(r) dr \tag{3}$$

where $D(r)$ is the pore-size distribution function. Assuming constant $\sigma$ and $\theta$, eq. 2 gives $$4 \quad p\, dr + r\, dp = 0 \tag{4}$$

Combining eqs. 3 and 4 gives $$5 \quad dV = -D(r)\,(r/p)\, dp \tag{5}$$

In an actual determination, the volume measured is that of all pores having radii greater than $r$. The total pore volume, $V_t$, is thus diminished by the volume, $V$, of pores smaller than $r$. A pressure-volume curve is therefore a plot of $(V_t - V)$ against $p$; its slope is $d(V_t - V)/dp$ or $-dV/dp$. Equation 5 may be rewritten in the form $$D(r) = \left(\frac{p}{r}\right)\frac{d(V_t - V)}{dp} \tag{6}$$

the right-hand terms of which are either known or determinable. For a number of values of $p$, the experimental pressure-volume curve may be differentiated to obtain $d(V_t - V)/dp$ while $r$ is calculated from eq. 2. Values for $D(r)$ are then found from eq. 6. Plotting $D(r)$ against $r$ gives the pore-size distribution.

Thus when $D(r)$ in cc/A is plotted against $r$ (radius of the pore) in A the radius will decrease as the value of $D(r)$ increases. At some position on the graph, however, a very large increase in $D(r)$ is accompanied by a very small, if any, decrease in the radius. The $r$ value corresponding to this point of radius stabilization indicates that a substantial number of pores has a radius of at least this value of $r$. It is this value which when converted to a diameter is herein defined as the average pore diameter.

Strongly acid or basic supports tend to catalyze unwanted side reactions and should be avoided. Further supports which tend to catalyze reactions, such as may occur between unsaturated-aldehyde and hydrogen, unsaturated aldehyde and unsaturated aldehyde, unsaturated aldehyde and its hydrogenation products or between the products themselves should also be avoided.

The supported rhenium catalyst comprises generally from about 0.01 to about 30%, typically from about 0.05 to about 25%, and preferably from about 0.70 to about 20% rhenium compound, and correspondingly generally from about 99.99 to about 70, typically from about 99.95 to about 75, and preferably from about 99.3 to about 80% by weight large pore diameter support based upon the total weight of the catalyst and support. The use of less than about 0.01% by weight rhenium compound may result in an effectively inactive catalyst whereas the use of more than about 30% by weight rhenium compound may result in pore blockage or uneconomical use of the expensive and valuable element (Re).

PREPARATION OF SUPPORTED RHENIUM CATALYST

The supported rhenium catalyst may be prepared in a variety of ways, as described more fully in copending patent application Ser. No. 685,596, filed on even data herewith and hereby incorporated by reference. These preparations should be carried out in the substantial absence of air, water and oxygen because the presence of such substances tends to result in the formation of oxidized Re species or species with hard to reduce Re—O bonds, the presence of which would tend to decrease the selectivity of the catalyst.

The catalyst support should therefore be treated to insure freedom from extraneous organic or inorganic substances which might interfere with the conversion reaction. Thus, the support for the rhenium compound is prepared by refluxing it with from about 75 to about 90% by weight concentrated nitric acid and from about 25 to about 10% by weight concentrated perchloric acid (based upon the total weight of the two acids) for a period of 240 minutes. The support is refluxed for from about 12 to about 24 hours with about 10 times its volume of doubly distilled water with frequent changes of the doubly distilled water. The support is then extracted several times with doubly distilled water and dried in oxygen gas. The temperature is then raised to 500° C under 1 atmosphere of oxygen gas and then cooled under nitrogen or helium gas.

In the practice of the present invention the rhenium containing compounds are thermally decomposed while present on the surface of catalyst support. Initially, the presence of the rhenium containing compounds on the surface of the support is provided through the process of adsorbtion without the aid of a chemical reaction. It is uncertain whether a reaction, sufficient to hold the catalyst containing compound even more firmly to the support than by adsorption alone, occurs under the subsequent conditions of decomposition and/or hydrogenation.

The rhenium containing compound may be deposited on the surface of the support by sublimation. More specifically, the rhenium compound is introduced into a break seal tube one end of which is connected to a vacuum source. The temperature is then reduced to at least 0° C (e.g., −78° C) while the pressure is reduced to about $10^{-4}$ to about $10^{-6}$ Torr. The other end of the break seal tube is connected to a larger tube which contains the catalytic support. The pressure of the support is also reduced to about $10^{-4}$ to about $10^{-6}$ Torr while the support is cooled to at least 0° C (e.g., −78° C) whereupon the seal of the break seal tube is broken. As the temperature of the rhenium compound is warmed to a temperature sufficient to volatilize the catalyst, which temperature may vary from about 0° C to about 100° C, it sublimes and migrates to the surface of the support upon which it condenses and is adsorbed by the support.

An alternative, and more preferred method of placing the rhenium compound on the surface of the support is achieved by the following procedure.

The rhenium compound is dissolved in tetrahydrofuran (hereinafter THF) or some other low boiling solvent (e.g., boiling point less than about 150° C at 14.7 psi) in which the rhenium compound is soluble and which is not easily reduced. Such alternative solvents include ethyl ether, toluene, and benzene. The solvent is preferably previously distilled under nitrogen gas in the presence of lithium aluminum hydride in order to remove any traces of water or peroxides which may be present. The solution of solvent and rhenium compound should be prepared in a nitrogen or inert gas atmosphere in order to avoid the presence of air water vapor, or peroxides.

The support, prepared as disclosed hereinabove, is then added to the solution of rhenium compound and solvent or the rhenium compound may be added to the support. While mechanically agitating the solution, the pressure is reduced until the solvent begins to boil at room temperature. At this time, the solution is repressurized with nitrogen gas or other inert gas. The pressure reduction step and repressurizing steps are then repeated 4 times. After 1 hour, the remaining solvent is removed and the supported rhenium catalyst is dried at room temperature under reduced pressure (1 millimeter of mercury).

The rhenium containing compound, having been adequately adsorbed on the surface of the catalyst support in the manner described is partially decomposed by pyrolyzing said compound at temperatures above about 125° C but below about 325° C in the presence of hydrogen gas. The hydrogen gas is present during the decomposition and is maintained at any positive pressure sufficient to minimize volatilization and loss of the rhenium compound. Representative positive pressures may vary from about 14.7 to about 10,000 psi while pressures which approach a high vacuum should be avoided.

Although, not essential, it is desirable to maintain a steady flow of $H_2$ over the catalyst support to allow for removal of carbon monoxide given off as part of the decomposition reaction and to maintain the absence of $O_2$. Too high a flow rate may undesirably result in excessive loss of the rhenium compound from the support. Flow rates should be sufficient to provide a contact time of about 10 to about 300 seconds. Thus, suitable flow rates may vary from about 50 to about 5000 standard cubic centimeters per minute (herein after SCCM), preferably from about 100 to 600 SCCM and most preferably from about 150 to about 450 SCCM. Such flow rates are pressure dependent and may be manipulated by one skilled in the art to achieve the desired contact time.

The reaction between the unsaturated aldehyde and the hydrogen-containing gas may be carried out at temperatures of generally from about 50° to about 250° C, typically from about 125° to about 200° C, and preferably from about 150° to about 175° C, and at pressures of generally from about 70 to about 10,000 psi (e.g., 70 to 7000 psi), preferably from about 100 to about 5000 psi, and most preferably from about 125 to about 1000 psi (e.g., 150 to 600 psi).

At temperatures substantially in excess of about 250° C, there may result decreased selectivity for the alpha-beta unsaturated alcohols with an accompanying increase in selectivity for saturated alcohols whereas at temperatures substantially less than about 50° C, there may result very low conversions.

Pressures substantially in excess of 10,000 psi are likely to result in unselective hydrogenation and increased use of expensive equipment whereas at pressures substantially less than about 70 psi, there may result a decrease in the reaction rates.

The process of the present invention is preferably carried out in the presence of a critical amount of a selective catalyst poison or a mixture of two or more such poisons. By "selective catalyst poison" is meant a compound which inhibits the conversion of unsaturated aldehyde to undesirable saturated by-products (e.g., propanol) but does not substantially interfere with the conversion of unsaturated aldehyde to the desired unsaturated product (e.g., allyl alcohol). Such selective catalyst poisons include carbon monoxide, carbon disulfide, hydrogen sulfide, methyl mercaptan, ethyl mercaptan, propyl mercaptan, carbonyl sulfide, thiophene, ethyl sulfide, propyl sulfide, and other sulfur containing compounds as well as compounds of selenium such as hydrogen selenide as well as compounds of tellurium, phosphorus, arsenic, lead and the like and mixtures thereof as long as the components of such mixtures do not react together. Carbon monoxide, carbon disulfide and mixtures thereof are preferred selective catalyst poisons.

The selective poison should be added in amounts sufficient to provide blockage of the sites which catalyze the formation of saturated compounds. Such amount may be achieved by initially introducing the selective catalyst poison in amounts of generally from about 0.001 to about 25 mole percent, typically from about 0.1 to about 15 mole percent and preferably from about 0.5 to about 5 mole percent based upon the total number of moles of reactants (i.e., alpha, beta-ethylenically unsaturated aldehyde plus hydrogen-containing gas) plus selective catalyst poison. When less than about 0.001 mole percent of certain selective catalyst poisons such as carbon monoxide are used, an insignificant effect may be observed. However, those poisons which are of low volatility and strongly bound to the active sites of the catalyst such as carbon disulfide will achieve the desired results even in amounts less than 0.001 mole percent but only over a much longer period of time. If more than about 25 mole percent of the selective catalyst poison is used, there may result a total inhibition of conversion of unsaturated aldehyde to any product.

It should be emphasized that the description of the ranges within which the amount of selective catalyst poison may vary has been tailored to meet the requirements of the specific system described herein in view of certain process parameters under which the reactions of the type also described herein are carried out. The amount of selective catalyst poison utilized is directly proportional to the number of active sites on the catalyst. Further, the selective catalyst poison begins to desorb from a given catalyst as the reaction temperature increases thereby requiring an increase in the partial pressure of the selective catalyst poison (i.e., increased concentration) in order to maintain, possibly through steric effects, the blockage or deactivation by the selective poison, of the sites responsible for the conversion of the unsaturated aldehyde to the saturated species. Thus, those selective catalyst poisons which are not readily desorbed at reaction conditions utilized herein such as carbon disulfides, do not have to be fed continuously into the reaction zone.

In addition to the steric effects noted above there may also be an electronic effect whereby a poison molecule present at a primarily saturated aldehyde producing site may increase or decrease the rate of reaction at a primarily unsaturated alcohol producing site, or change that site's relative selectivity.

Although I do not wish to be limited by any particular theoretical explanation it is believed that the selective catalyst poison is more strongly complexed or held on the rhenium than the carbon-carbon double bond of the alpha, beta-ethylenically unsaturated aldehyde, but somewhat less strongly held than the carbonyl group of the alpha, beta-ethylenically unsaturated aldehyde thereby resulting in a reduction of carbon-carbon double bond hydrogenation, and having little effect on the carbonyl group hydrogenation.

The process of the present invention may be practiced either by passing the feed mixture through a fixed catalyst bed or through a reactor wherein the catalyst is present in finely divided form and is maintained in the "fluidized" state by the upward passage therethrough of the gaseous reactants. The process is most conveniently carried out in a continuous manner, although semi-continuous or batch processes may also be employed. In the preferred method of continuous operation, the components of the feed stream may be brought together and, under the desired pressure, passed in the vaporous condition through a suitable catalyst heated to the desired temperature. The reaction zone advantageously is an elongated tube or tubes wherein the catalyst is positioned. The feed may be brought into the catalyst in either an unheated or preheated condition. The effluent from the reactor may then be separated into its various constituents by conventional means, the most convenient of which is that of fractional distillation. If desired, any unconverted portion of the unsaturated aldehyde or unsaturated aldehyde mixture present in the effluent may be recirculated through the catalyst in the reactor, preferably admixed with fresh feed gases.

In the present process, the hydrogen-containing gas, plus any selective catalyst poison (such as carbon monoxide), plus any internal standard (such as ethane) that may be used may be bubbled through the liquid unsaturated aldehyde or mixture thereof dissolved in an inert solvent held under the appropriate temperature to maintain the unsaturated aldehyde in the vapor phase and the reactant gas mixture may then be sent to a reactor.

Alternatively, the selective catalyst poison may be added, after contact of the alpha, beta-ethylenically unsaturated aldehyde with the hydrogen gas but prior to reaction in a manner sufficient to achieve even mixing.

If the selective catalyst poison is a liquid it may be heated to achieve a vapor pressure sufficient to assure that an adequate amount of the selective poison will be present in the gas stream. The need for additional selective poisons may be determined by monitoring the identity of the products using gas chromatographic analysis and adjusting the selective poison feed to achieve the desired selectivity.

The reactors useful in the present invention may be of varying dimensions. A preferred reactor for laboratory scale preparation is a cylindrical reactor which is about 30 centimeters long with an internal diameter of 0.5 centimeter, and which has a volume of about 6 cubic centimeters. This reactor may have a fine screen at the bottom of the cylinder to contain the catalyst particles which may be present throughout the reactor.

The gaseous products are then passed through the reactor to a pressure reduction valve and then to a gas chromatograph for analysis.

The rate at which the feed gases may be passed through the heated catalyst bed should be sufficient to provide a period of contact between the reactants and catalyst which may vary from about 0.1 to about 50 seconds, preferably from about 0.5 to about 25 seconds, and most preferably 1 to about 15 seconds. A period of contact in excess of 50 seconds may lead to decreased selectivity while very short periods of contact (e.g., less than 0.1 seconds) may lead to very low conversion.

In the absence of a selective catalyst poison, the present process results in a conversion of unsaturated aldehydes of generally greater than about 1.7%, typically greater than about 9%, and preferably greater than about 30%, and a selectivity to alpha, beta-ethylenically unsaturated alcohol of generally greater than about 50%, typically greater than about 55%, and preferably greater than about 60%.

When a selective catalyst poison is used in the process of the present invention, there is an increase in the selectivity to alpha, beta-ethylenically unsaturated alcohol at the expense of conversion of unsaturated aldehyde. Thus, there results a conversion of unsaturated aldehyde of generally greater than about 1%, typically greater than about 5%, and preferably greater than about 8%, and a selectivity to alpha, beta-ethylenically unsaturated alcohol of generally greater than about 60%, typically greater than about 63%, and preferably greater than about 80%.

It has been found that as temperature increases, the conversion of unsaturated aldehyde increases but the selectivity to alpha, beta-ethylenically unsaturated alcohol decreases. Certain catalysts such as those disclosed in U.S. Pat. No. 2,763,696 (Finch et al) and U.S. Pat. No. 2,767,221 (Ballard et al.). are only active at temperatures in excess of 200° C thus resulting in poor selectivity while other catalysts such as those disclosed in U.S. Pat. No. 3,655,777 (Rylander et al) utilize catalysts which function at lower temperatures but are extremely expensive and toxic. The catalysts useful in the present process are active at temperatures of 250° C, and temperatures substantially less than 250° C. Thus, by using such low temperatures, a significant increase in selectivity over prior art catalysts may be observed as well as the economic advantages resulting from the use of lower temperatures.

The alpha, beta-ethylenically unsaturated alcohols produced in the present process may be used as a co-monomer in certain compounds such as acrylic based photo polymerized polymers. These alcohols may also be used in preparing esters for use in resins and plasticizers. Allyl alcohol may be used in the preparation of glycerol, tetrahydrofuran, gamma-butyrolactone, 2l-methyl-1,3-propane diol and 1,4-butane diol. 1,4-butane diol is a component in polyurethane and polybutylene terephthalate materials.

The present invention is further illustrated by the following examples. All parts are on a mole basis while percentages in the examples as well as in the specification and claims are by weight unless otherwise specified

EXAMPLE I $Re_2CO_{10}$ is sublimed into carefully cleaned 126 A controlled pore size type pore glass in the absence of oxygen and found to contain 0.9% Re by weight. The rhenium containing catalyst support is transferred to a reactor where it is partially decomposed by heating to 282° C under 305 psi $H_2$ at a flow rate of 450 SCCM. The support is then exposed to 18.5 mole percent $CS_2$ in $H_2$ at 280° C and cooled over the course of 2 hours to 200° C. At this temperature and at a total pressure of 289 psi a hydrogen:acrolein vaporous mixture with a feed ratio of 64:1 is passed through the reactor at a flow rate of 450 SCCM and a contact time of 24 seconds. 1.7% of the acrolein is converted and the observed product composition was 89.4% allyl alcohol, 6.4% propanal, and 4.2% propanol.

EXAMPLE II $Re_2CO_{10}$ is absorbed from dry oxygen free tetrahydrofuran solution onto carefully cleaned 126 A controlled-pore size type pore glass to give 10 ml of an 11.2% Re by weight catalyst. Under nitrogen this catalyst is dried and loaded into a reactor tube. The tube is installed in a suitable reactor assembly and the catalyst partially decomposed with 99.995% $H_2$ at 300° C 165 psi under a flow rate of 150 SCCM. A gaseous mixture of hydrogen and acrolein at a ratio of 72:1 is passed through the reactor under a pressure of 321 psi a temperature of 150° C, a 450 SCCM flow rate and a contact time of 27.9 seconds. 14.9% of the acrolein is hydrogenated with a selectivity of 53.8% to allyl alcohol, 33.6% to propanal and 10.6% to propanol. On X-ray examination after use, this catalyst was found to have sharp lines at 2.39, 2.23, 2.11, 1.63, 1.38, 1.26, 1.19, 1.17, and 1.15 A ascribable to the presence of Re crystallites.

EXAMPLE III

The same catalyst as above is fed 35 parts $H_2$ and 1 part acrolein and about 1 part $CS_2$ at 225° C, 164 psi with a flow rate of 250 SCCM and a contact time of 24 seconds. 8.7% of the acrolein is hydrogenated with a selectivity of 63.5% allyl alcohol, 8.7% propanal, and 9.8% propanol.

EXAMPLE IV

The same catalyst as in Example II, but after 30 days storage under $N_2$, is loaded into a reactor tube and placed under 165 psi $H_2$ at a flow rate of 150 SCCM. The temperature is increased over the course of 5 hours from 20° to 300° C and then the gas feed is changed to 99% He and 1% $H_2$ as the catalyst is allowed to cool over 10 hours back to 20° C. The reactor is then fed 47 parts $H_2$ and 1 part acrolein at 215 psi, and 175° C with a flow rate of 450 SCCM and contact time of 17.8 seconds. 22.6% of the acrolein is hydrogenated with a selectivity of 51.8% allyl alcohol, 28.0% propanal, 15.8% propanol with 4.4% unidentified higher boiling by-products also being produced. When this catalyst is fed a hydrogen acrolein blend with a ratio of 118:1 at 517 psi, at a flow rate of 450 SCCM, a contact time of 44.5 seconds, at a temperature of 126° C, 12.7% of the acrolein is hydrogenated with a selectivity of 59.2% allyl alcohol, 33.5% propanal and 12.3% propanol.

EXAMPLE V

The same catalyst as in the previous example is fed 114 parts hydrogen, 1 part carbon monoxide and 1 part acrolein at 505 psi at a temperature of 126° C at a flow rate of 450 SCCM and contact time of 43.6 seconds. 1.8% of the acrolein was hydrogenated with a selectivity of 63.8% allyl alcohol, 25.3% propanal and 10.9% propanol. When the reactor temperature is increased to 150° C the acrolein conversion to hydrogenated products increased to 8.6% with a selectivity of 57.5 allyl alcohol, 32.4 % propanal and 10.1% propanol.

EXAMPLE VI

The same catalyst as in Example IV is fed 116 parts hydrogen, 2 parts carbon disulfide and 1 part acrolein at 150° C at 517 psi at a flow rate of 450 SCCM and contact time of 44.6 seconds. 9.0% of the acrolein is hydrogenated with a selectivity of 60.9% allyl alcohol, 32.8% propanal and 6.3% propanol.

EXAMPLE VII $Re_2CO_{10}$ is absorbed from a dry, oxygen free tetrahydrofuran solution onto 10 grams of carefully cleaned 215 A average pore diameter controlled pore size type pore glass. The Re containing glass was dried under nitrogen to yield a 17.3% Re catalyst which under nitrogen is loaded into a 10 ml reactor tube. During decomposition the catalyst is heated to 200° C over the course of 2.4 hours while under 215 psi $H_2$ flowing at 150 SCCM. The temperature is then increased to 300° C for 5 hours under the same pressure and flow conditions. The catalyst is slowly cooled to room temperature under 99% He and 1% $H_2$ at 215 psi, 150 SCCM. 73 parts $H_2$ to 1 part acrolein is then passed over this catalyst at 175° C, 326 psi at a flow rate of 750 SCCM and contact time of 16.6 seconds. 37.9% of the acrolein is hydrogenated with a selectivity of 52.8% allyl alcohol, 33.8% propanal and 13.4% propanol.

EXAMPLE VIII

Comparative Example Using $Re_2O_7$ 5.54 grams of carefully cleaned controlled pore size type pore glass with a mean pore diameter of 215 A and a pore distribution of ± 5.6% is transferred to $N_2$ dry box and mixed with 1 gram of Ventron $Re_2O_7$ and 50 ml of redistilled tetrahydrofuran. The mixture is stirred under pulsed 20″ Hg vacuum until dryness, loaded into reactor tube and treated for 2.4 hours at 300° C under 215 psi $H_2$ flowing at 150 SCCM and contact time of 12.9 seconds. The resulting catalyst had 13% Re by weight after use. When this catalyst is fed a mixture of 98% $H_2$ and 2% acrolein at 252 psi flowing at a rate of 750 SCCM, at a temperature of 154° C, 19.7% of the acrolein is converted to products. The product composition of 44.6% allyl alcohol and 55.4% propanol.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

I claim:

1. A selective vapor phase process for preparing alpha, beta-ethylenically unsaturated alcohols which comprises reacting at least one alpha, beta-ethylenically unsaturated aldehyde with a hydrogen-containing gas in the vapor phase in the presence of a supported rhenium catalyst comprising (I) at least one rhenium compound having a formal oxidation number on the rhenium atom of three or less, and (2) at least one support for said rhenium compound, said support having an average pore diameter greater than about 40 A 2. The process of claim 1 wherein said supported rhenium catalyst comprises from about 0.05 to about 25% by weight of at least one rhenium compound and from about 99.95 to about 75% by weight of at least one support which is selected from the group consisting of activated carbon, silica, controlled pore size type pore glass, controlled pore size type ceramics, and mixtures thereof.

3. The process of claim 2 wherein said reaction is carried out at temperatures of from about 50° to about 250° C, and at pressures of from about 70 to about 7000 psi.

4. The process of claim 3 wherein said alpha, beta-ethylenically unsaturated aldehyde and hydrogen-containing gas are reacted in a molar ratio of hydrogen gas to unsaturated aldehyde of from about 1 to 1 to about 200 to 1.

5. A selective vapor phase process for preparing alpha, beta-ethylenically unsaturated alcohols which comprises: reacting at least one alpha, beta-ethylenically unsaturated aldehyde with a hydrogen-containing gas in the vapor phase in the presence of a supported rhenium catalyst comprising;
I. a catalyst support having a plurality of pores with an average pore diameter of at least 40 A which is substantially inert toward alpha, beta-ethylenically unsaturated aldehydes or alpha, beta-ethylenically unsaturated alcohols at temperature and pressure conditions utilized in preparing the alpha, beta-ethylenically unsaturated alcohols, and having present on the pore surface thereof,
II. The product resulting from thermally decomposing a rhenium-containing compound having the initial structure selected from the group consisting of $Re_2(CO)_{10}$, $\pi$-$C_5H_5(CO)_3$, $\pi$-$(C_5H_5)_2ReH$, $C_{10}H_{11}Re(CO)_2$ and $RReILO)_5$ wherein R is a radical selected from the group consisting of phenyl, methyl, and perfluropropyl, to an extent sufficient to provide a plurality of coordination vacancies on the surface of said product which are capable of inducing the selective conversion of said alpha, beta-ethylenically unsaturated aldehydes, which thermal decomposition is achieved by
a. adsorbing said rhenium-containing compounds on the surface of said catalyst support,
b. heating the catalyst support having the rhenium-containing compounds adsorbed thereon at a temperature of about 125° to 325° C in the presence of a hydrogen-containing gas while maintaining a positive pressure.

6. The process of claim 5 wherein the supported rhenium catalyst has a selective catalyst poison, selected from the group consisting of carbon monoxide, carbonyl sulfide, carbon disulfide, methyl mercaptan, ethyl mercaptan, propyl mercaptan, hydrogen sulfide, thiophene, ethyl sulfide, propyl sulfide, hydrogen selenide, and mixtures thereof, present on the surface thereon in an amount sufficient to selectively inhibit the formation of saturated by-products.

7. The process of claim 5 wherein said reaction is carried out at temperatures of from about 50° to about 250° C, and at pressures of from about 100 to about 5000 psi.

8. The process of claim 5 wherein said alpha, beta-ethylenically unsaturated aldehyde and hydrogen-containing gas are reacted in a molar ratio of hydrogen gas to unsaturated aldehyde of from about 1 to 1 to about 200 to 1.

9. The process of claim 5 wherein the rhenium-containing compound which is thermally decomposed is $Re_2(CO)_{10}$.

10. The process of claim 5 wherein said catalyst composition comprises from about 0.05 to about 25% by weight of at least one thermally decomposed rhenium-containing compound and from about 99.95 to about 75% by weight of a support which is selected from the group consisting of activated carbon, silica, controlled pore size type glass, and mixtures thereof.

11. The process of claim 10 wherein said reaction is carried out at temperatures of from about 125° to about 225° C, and at pressures of from about 125 to about 1000 PSI.

12. The process of claim 11 wherein said catalyst support contains pores having average pore diameters greater than about 100 A.

13. A selective vapor phase process for preparing alpha, beta-ethylenically unsaturated alcohols which process comprises reacting at least one alpha, beta-ethylenically unsaturated aldehyde with a hydrogen-containing gas in a molar ratio of hydrogen gas to unsaturated aldehyde of from about 1 to 1 to about 200 to 1 in the vapor phase at temperatures of from about 150° to about 175° C, and at pressures of from about 150 to about 600 psi, in the presence of (I) a supported catalyst comprising (1) from about 99.3 to about 80% by weight based on the total weight of catalyst and support of at least one support which may be selected from the group consisting of activated carbon, silica, and controlled pore size type pore glass having an average pore diameter of at least about 40 A, and mixture thereof, (2) from about 0.7 to about 20% by weight of at least one rhenium-containing compound which is a product resulting from thermally decomposing rhenium decacarbonyl having the initial structure $Re_2(CO)_{10}$, to an extent sufficient to provide a plurality of coordination vacancies on the surface of said product which are capable of inducing the selective conversion of said alpha, beta-ethylenically unsaturated aldehydes, which thermal decomposition is achieved by a. absorbing said rhenium decacarbonyl on the surface of said catalyst support.

b. heating the catalyst-support having the rhenium decacarbonyl absorbed thereon at temperatures which may vary from about 125° C to 325° C in the presence of a hydrogen-containing gas while maintaining a pressure of at least 14.7 psi, and II. from about 0.5 to about 5 mole percent of a selective catalyst poison based on the total number of moles of reactant and selective catalyst poison which inhibits the formation of saturated byproducts, but does not inhibit the formation of unsaturated alcohols, said selective catalyst poison being selected from the group consisting of carbon monoxide, carbon disulfide, hydrogen sulfide, methyl mercaptan, ethyl mercaptan, propyl mercaptan, thiophene, ethyl sulfide, propyl sulfide, hydrogen selenide, and mixtures thereof.

14. The process of claim 13 wherein the support material is silica and the selective catalyst poison is selected from the group consisting of carbon monoxide, carbon disulfide, and mixtures thereof.

* * * * *